United States Patent [19]

Rottloff et al.

[11] 4,046,796
[45] Sept. 6, 1977

[54] PROCESS FOR THE PRODUCTION OF POLYFUNCTIONAL CYANIC ACID ESTERS

[75] Inventors: Günther Rottloff, Cologne; Rudolf Sundermann, Leverkusen; Ernst Grigat, Odenthal-Gloebusch; Rolf Pütter, Duesseldorf, all of Germany

[73] Assignee: Bayer Aktiengesellschaft, Germany

[21] Appl. No.: 658,815

[22] Filed: Feb. 17, 1976

[30] Foreign Application Priority Data

Feb. 22, 1975 Germany ............................ 2507705
July 2, 1975 Germany ............................ 2529487

[51] Int. Cl.$^2$ ............................................ C07C 122/00
[52] U.S. Cl. ........................ 260/453 P; 260/453 AR; 260/463
[58] Field of Search ................................... 260/453 P

[56] References Cited

U.S. PATENT DOCUMENTS

| 3,107,261 | 10/1963 | Gerber et al. | 260/453 |
| 3,553,244 | 1/1971 | Grigat et al. | 260/453 |
| 3,595,900 | 7/1971 | Loudas et al. | 260/453 |

Primary Examiner—Dolph H. Torrence
Attorney, Agent, or Firm—Connolly and Hutz

[57] ABSTRACT

Highly pure aromatic polyfunctional cyanic acid esters having a high stability in storage and being extraordinary suitable for use as starting compound for the production of plastics by cyclopoly-trimerization are obtained by a special process. Alkaline earth and/or alkali metal salts of polyfunctional aromatic hydroxy compounds said alkaline earth and/or alkali metal compound capable of phenolate formation are used in excess of up to 0.1 mol per mol of aromatic hydroxy group are reacted with an excess of cyanogen halide. The cyanogen halide excess comprises up to 1 mol per mol of aromatic hydroxy group plus excess mol of the metal compound used for salt production.

2 Claims, No Drawings

PROCESS FOR THE PRODUCTION OF POLYFUNCTIONAL CYANIC ACID ESTERS

This invention relates to a process for the production of highly pure, aromatic polyfunctional cyanic acid esters having a high stability in storage.

It is known that monophenols or polyphenols, optionally attached to a heterocyclic radical, carrying at most one sterically hindering substituent in the ortho positions relative to each hydroxyl group, can be reacted with halogen cyanides and a tertiary amine (molar ratio 1:1:1) in an inert organic medium at temperatures below 65° C (DT-PS No. 1,195,764).

It is also known that aromatic cyanic acid esters can be obtained by using an inorganic base which is capable of phenolate formation under the reaction conditions instead of a tertiary amine (DT-PS No. 1,248,668).

In addition, it is known from DT-PS No. 1,248,667 that phenols can be reacted with halogen cyanides and a base capable of phenolate formation under the reaction conditions at temperatures below 65° C in the presence of water and/or an alcohol or alcohol mixture as a solvent. In many cases, the polyfunctional cyanic acid esters obtained by these processes do not have the requisite purity and stability in storage, so that they are not really suitable for use as starting compounds for the production of plastics (for example in accordance with DT-AS No. 1,190,184).

By contrast, it is already known that the reaction of phenolates with cyanogen halides gives trimeric products, mainly in the form of triazine derivatives, which are formed by way of the imino carbonic acid phenyl esters, the latter also being formed as a reaction product (Liebigs Ann. Chem. Vol. 287, page 319 and Ber. detsch. Ges., Vol. 28, page 2467).

It has now been found that highly pure polyfunctional aromatic cyanic acid esters can be obtained in high yields by reacting the alkali or alkaline earth metal salts of aromatic di- or poly-hydroxy compounds with halogen cyanides in a solvent, optionally in the presence of catalytic quantities of a tertiary amine.

Aromatic di- or poly-hydroxy compounds, which may be used as starting compounds for the process according to the invention, are known in large numbers. It is possible in accordance with the invention to use virtually any aromatic and aromatic-heterocyclic, optionally substituted compounds containing two or more phenolic hydroxy groups, providing the substituents, if any, are stable and do not themselves react under the conditions of the process according to the invention.

The aromatic hydroxy compounds preferably correspond to the general formula (I):

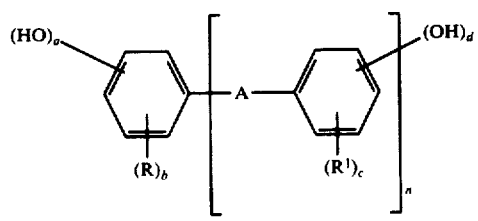

(I)

in which
$a$ is the number 1, 2 or 3;
$b = 5 - a$;
$c = 5 - d$;
$d =$ the number 1, 2 or 3,
the sum of $a$ and $d$ ($a + d$) being a number from 2 to 4, preferably the number 2 or 3, more especially the number 2, where $n = 0$; and a number from 2 to 6, preferably a number from 2 to 4, more especially the number 2, where $n = 1$;

$n$ is 0 or 1; and

R has the meaning defined under formula (II), whilst A and $R^1$ have the meaning defined under formula (III). In particular the aromatic hydroxy compounds which may be used in the process according to the invention correspond to the general formula (II):

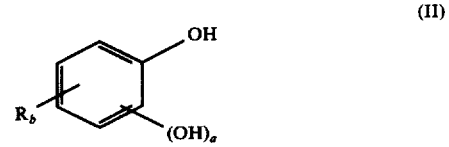

(II)

in which
R represents hydrogen, halogen, alkyl or phenyl; several radicals R do not have to be the same or two radicals R which substitute adjacent carbon atoms may even form with those carbon atoms a carbocyclic or heterocyclic 5-membered or 6-membered ring;

$a$ is the number 1, 2 or 3; and
$b = 5 - a$.

$a$ is preferably the number 1 or 2, more especially the number 1.

Of the radicals R, one or two, more especially one, preferably has a meaning other than hydrogen, whilst the others represent hydrogen.

Another group of the aromatic di- and poly-hydroxy compounds which may be used in the process according to the invention correspond in particular to the formula (III):

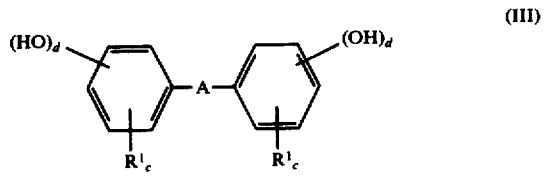

(III)

in which
A represents oxygen, the sulphonyl group (—$SO_2$—), the carbonyl group (—CO—), the carbonyl dioxy group

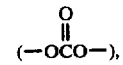

(—OCO—), sulphur (—S—), a $CH_2$-chain having from 1 to 9 and preferably from 1 to 6 carbon atoms optionally substituted by other alkyl radicals, preferably methyl, or phenyl, a cycloaliphatic or aromatic 5-membered or 6-membered ring or a single bond;
$R^1$ has the meaning defined above for R or represents the group (IV):

(IV)

-continued

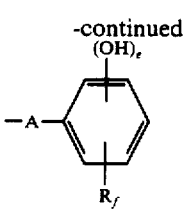

in which
A and R are as defined above,
e is the number 1, 2 or 3, and
f = 5 − e;
c = 5 − d; and
d is the number 1, 2 or 3.
d and e preferably represent the numbers 1 or 2, more especially the number 1.

$R^1$ preferably has the same meaning as R.

Of the $c^1$ radicals $R^1$ and $f^1$ radicals R, one or two radicals, more especially one radical, preferably has a meaning other than hydrogen, whilst the others represent hydrogen.

Of the halogens (fluorine, chlorine, bromine and iodine), fluorine, chlorine and bromine are preferred.

Suitable alkyl radicals are straight-chain or branched alkyl radicals having from 1 to 9 carbon atoms and preferably from 1 to 5 carbon atoms, for example methyl, ethyl, propyl, isopropyl, n-butyl, isobutyl, t-butyl and the isomeric pentyl radicals, more especially methyl, ethyl and t-butyl.

The following are mentioned as examples of compounds corresponding to general formula (I) above: m-, p-dihydroxy benzene, 2-tert.-butyl hydroquinone, 2, 4-dimethyl resorcinol, 2, 5-di-tert.-butyl hydroquinone, tetramethyl hydroquinone, 2,4,6-trimethyl resorcinol, 2,6-di-tert.-butyl hydroquinone, 4-chlororesorcinol, and dihydroxy naphthalenes such as, for example, 1,4-, 1,5-, 1,6-, 1,7-, 2,6- and 2,7-dihydroxy naphthalene.

The following are mentioned as examples of compounds corresponding to general formula (II) above:

dihydroxy diphenyls such as for example 4,4'-dihydroxy diphenyl, 2,2'-dihydroxy diphenyl, 3,3',5,5'-tetramethyl-4,4'-dihydroxy diphenyl, 3,3',5,5'-tetrachloro-4,4'-dihydroxy diphenyl, 3,3',5,5'-tetrachloro-2,2'-dihydroxy diphenyl, 2,2',6,6'-tetrachloro-4,4'-dihydroxy diphenyl, 4,4'-bis-[(3-hydroxy)-phenoxy]-diphenyl, 4,4'-bis-[(4-hydroxy)-phenoxy]-diphenyl; 2,2'-dihydroxy-1,1'-binaphthyl; dihydroxy diphenyl ethers, such as for example 4,4'-dihydroxy diphenyl ether, 3,3',5,5'-tetramethyl-4,4'-dihydroxy diphenyl ether, 3,3',5,5'tetrachloro-4,4'-dihydroxy diphenyl ether, 4,4'-bis-[p-hydroxy phenoxy]-diphenyl ether, 4,4'-bis-[p-hydroxy phenyl isopropyl]-diphenyl ether, 4,4'-bis-[p-hydroxy phenoxy]-benzene, 4,4'-bis-[m-hydroxy phenoxy]-diphenyl ether, 4,4'-bis-[4-(4-hydroxy phenoxy)-phenyl sulphone]-diphenyl ether; diphenyl sulphones, such as for example 4,4'-dihydroxy diphenyl sulphone, 3,3',5,5'-tetramethyl-4,4'-dihydroxy diphenyl sulphone, 3,3',5,5'-tetrachloro-4,4'-dihydroxy diphenyl sulphone, 4,4'-bis-[p-hydroxy phenyl isopropyl]-diphenyl sulphone, 4,4'-bis-[(4-hydroxy)-phenoxy]-diphenyl sulphone, 4,4'-bis-[(3-hydroxy)-phenoxy]-diphenyl sulphone, 4,4'-bis-[4(4-hydroxy phenyl isopropyl)-phenoxy]-diphenyl sulphone, 4,4'-bis-[4-(4-hydroxy phenyl sulphone)-phenoxy]-diphenyl sulphone, 4,4'-bis-[4-(4-hydroxy)-diphenoxy]-diphenyl sulphone; dihydroxy diphenyl alkanes, such as for example 4,4'-dihydroxy diphenyl methane, 4,4'-bis-[p-hydroxy phenyl]-diphenyl methane, 2,2-bis-(p-hydroxy phenyl)-propane, 2,2-bis-(3,5-dimethyl-4-hydroxy phenyl)-propane, 2,2-bis-(3,5-dichloro-4-hydroxy phenyl)-propane, 1,1-bis-[p-hydroxy phenyl]-cyclohexane, bis-[2-hydroxy-1-naphthyl]-methane, 1,2-bis-[p-hydroxy phenyl]-1,1,2,2-tetramethyl ethane, 4,4'-dihydroxy benzophenone, 4,4'-bis-(4-hydroxy)-phenoxy benzophenone, 1,4-bis-[p-hydroxy phenyl isopropyl]-benzene, phloroglucinol and 2,2',5,5'-tetrahydroxy diphenyl sulphone.

Lithium, sodium, potassium, rubidium, caesium, calcium, barium and strontium are mentioned as alkali or alkaline earth metal components of the phenolates. Sodium, potassium, calcium and barium are preferably used.

Cyanogen chloride or cyanogen bromide, both of which are readily obtainable, are particularly suitable for use as the cyanogen halide.

The following solvents, for example, may be used: water; lower aliphatic alcohols such as methanol, ethanol, propanol, isopropanol and butanol; ketones such as acetone and methylethyl ketone; amides such as dimethyl formamide and dimethyl acetamide; cyclic ethers such as dioxane and tetrahydrofuran; or mixtures thereof, more especially a mixture of isopropanol and water.

Tertiary amines which may be used in catalyctic quantities for the process according to the invention preferably correspond to the general formula:

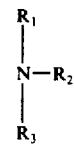

in which
$R_1$, $R_2$ and $R_3$ represent alkyl radicals having from 1 to 36 carbon atoms, more especially up to 18 carbon atoms, aryl radicals such as phenyl and cycloalkyl radicals having from 4 to 7 carbon atoms, more especially from 5 to 6 carbon atoms, or cycloalkyl radicals having 6 carbon atoms which are interrupted by $C_1$ to $C_4$-alkylene groups and which do not have to be the same as one another (for example trimethyl amine, triethyl amine, methyl diethyl amine, tripropyl amine, tributyl amine, methyl dibutyl amine, dinonyl methyl amine, dimethyl stearyl amine, dimethyl cyclohexyl amine and diethyl aniline.

In general, the tertiary amines are used in a quantity of from 0.001 to 10% by weight and more especially in a quantity of from 0.001 to 1.0% by weight, based on the di- or poly-alkali or alkaline earth metal phenolates. However, the presence of the tertiary amines is not absolutely essential.

One process for the production of the phenolate compounds used in the process according to the invention is generally known. The aromatic di- or poly-hydroxy compounds described above are reacted with alkali or alkaline earth metal compounds which are capable of phenolate formation. An excess of up to 0.1 mol of the inorganic base per mol of phenolic hydroxyl group to be reacted is used in this reaction. The phenolate obtained may be isolated or may be reacted directly with the cyanogen halide, i.e. without previous isolation.

Further reaction of the phenolate thus prepared with the cyanogen halide is carried out in such a way that an excess of cyanogen halide is used based on the sum of the mols of the phenolate groups used plus the excess alkaline earth or alkali metal compounds used for and still present after their production. The excess can amount to 1 mol although it preferably amounts to 0.4 mol, based on 1 mol of phenolate groups plus excess mols of alkali or alkaline earth metal compounds.

In cases where, in addition to the reaction of the phenolate with the cyanogen halide, a tertiary amine is used as a catalyst, the cyanogen halide has to be used in an excess based on the sum of the phenolate groups used plus the excess of the alkaline earth or alkali metal compounds plus the tertiary amine.

This is illustrated by the following calculation:
 a. The reaction to form a phenolate was carried out for example by reacting 1 mol of a dihydroxy compound with 2.2 mols of an alkali metal compound. The diphenolate formed is subsequently reacted with 4.2 mols of cyanogen halide (2.2 mols per alkali metal compound plus 1 mol per phenolate group = 4.2 mols of cyanogen halide).
 b. Where 10% by weight of a catalyst (tertiary amine) is used, 11% by weight of cyanogen halide, based on the di- or poly-alkali or alkaline earth metal phenolate, has to be additionally added. The reaction may be carried out at temperatures in the range of from $-40°$ to $+65°$ C and is preferably carried out at temperatures in the range of from $0°$ to $30°$ C. In cases where cyanogen chloride is used, the reaction is preferably carried out at a temperature below its boiling point ($13°$ C), although where cyanogen bromide is used it is even possible to apply temperatures in the upper part of the above-mentioned temperature range, for example temperatures above $50°$ C.

The process according to the invention is generally carried out by reacting the di- or poly-alkali or alkaline earth metal phenolate solution, optionally provided with a catalyctic quantity of a tertiary amine, with the cyanogen halide. The polyfunctional aromatic cyanic acid ester formed may readily be isolated by known methods, such as filtration, vacuum filtration or centrifuging.

The process according to the invention is particularly suitable for continuous working. In this case, the phenolate solution and the cyanogen halide are pumped continuously into a mixing chamber in which the cyanic acid ester is immediately formed.

The aromatic polyfunctional cyanic acid esters are valuable starting materials for the production of plastics. They may be polymerised by known methods, such as the method described in DT-AS No. 1,190,184, to form high molecular weight polytriazines which may be used in various fields, for example as fibre-reinforced plastics, moulding or casting resins, adhesives, coating compositions or lacquers.

It must be regarded as particularly surprising that highly pure polyfunctional cyanic acid esters can be obtained by the process according to the invention. Minor impurities, such as unreacted starting compounds and/or aromatic hydroxy compounds reacted at one OH-group only, and also iminocarbonic acid esters have an extremely adverse effect upon the stability of the monomers in storage and upon their processibility into polytriazines. Thus, polyfunctional cyanic acid esters having an adequate stability in storage are frequently impossible to obtain in accordance with the prior art. In addition, these cyanic acid esters previously obtained are frequently very difficult to process because the impurities act as polymerisation activators so that the cyanic acid esters frequently polymerise too quickly and exothermically. The result is that the heat of reaction cannot always be uniformly dissipated and this, in some cases, can result in complete destruction of the polymers.

The invention is illustrated by, but by no means limited to, the following Examples in which the percentages quoted are by weight.

EXAMPLE 1

54 g (0.88 mol) of cyanogen chloride are introduced at $-5°$ C into 550 ml of isopropanol in a 2 liter stirrer-equipped vessel provided with a thermometer and a dropping funnel. A solution of 32.3 g (0.808 mol) of sodium hydroxide, 91.2 g (0.4 mol) of 2,2-bis-(p-hydroxy phenyl)-propane and 0.9 g of triethyl amine in 520 ml of water is added dropwise with stirring and cooling through a dropping funnel at such a rate that the reaction temperature can be kept at $-5°$ to $+3°$ C. On completion of the reaction, the reaction mixture has a pH-value of 6 to 7. The dicyanate precipitated is filtered under suction and washed with water until free from chloride. It is then washed with $3 \times 50$ ml portion of isopropanol and dried in a stream of air. Yield: 102 g (92% of the theoretical), m.p.: $82°$ C, $n_D^{90}$: 1.5385.

The pure dicyanate obtained according to Example 1 polytrimerises within 18 hours at $150°$ C up to conversion of 48% of the theoretical and is extraordinarily suitable as starting compound for the production of plastics in accordance with DT-AS No. 1,190,184. Contrary thereto, the same dicyanate obtained according to the process of DT-PS No. 1,195,764 or DT-PS No. 1,248,668 poly-tri-merises within 1 to 5 hours up to a conversion of 48% in a uncontrollable and strongly exothermic reaction.

EXAMPLE 2

For the continuous production of the dicyanate of 2,2-bis-(p-hydroxy phenyl)-propane (bisphenol A), a solution was prepared from 1824 g (8 mols) of bisphenol A, 659 g (16.5 mols) of sodium hydroxide, 18 g of triethyl amine and 9860 g of water. In addition, 1180 g (19.2 moles) of cyanogen chloride (120%, based on bisphenol A) and 8440 g of isopropanol precooled to $5°$ C were added. Both solutions were introduced into measuring vessels cooled with iced water and, by means of a metering pump, were sprayed synchronously through capillaries into a reaction vessel (capacity 500 ml) equipped with a jacket cooling system, a powerful stirrer and an overflow. The reaction temperature was kept by cooling at $-5°$ to $+3°$ C. The crystalline sludge formed was continuously filtered off under suction and washed with 500 ml of a water: isopropanol mixture (1:1) per kilogram of bisphenol-A-dicyanate. The filter residue was then washed with water until free from chloride. 2030 g (92% of the theoretical) of dicyanate were obtained after drying in a stream of air at $35°$ C. m.p.: $82°$ C, $n_D^{90}$: 1.5385.

The dicyanate obtained poly-trimerises within 26 hours at $150°$ C up to conversion of 48% of the theoretical.

EXAMPLE 3

A solution of 1824 g (8 mols) of 2,2-bis-(4-hydroxy phenyl)-propane, 922 g (16.5 mols) of KOH and 18 g of triethyl amine in 5.2 kg of water is synchronously reacted as described in Example 2 with a cooled mixture of 1180 g (19.2 mols) of cyanogen chloride and 4800 g of isopropanol at a temperature of −5° to +3° C. The crystalline sludge formed is worked up in the same way as described in Example 2. The yield amounts to 2020 g (approximately 92% of the theoretical) of dicyanate. m.p.: 82° C, $n_D^{90} = 1.5385$.

EXAMPLE 4

75 ml of isopropanol and 27 g (0.44 mol) of cyanogen chloride are introduced at −5° C into a 1 liter capacity stirrer-equipped flask. A solution, prepared under nitrogen, of 22 g (0.2 mol) of resorcinol, 16.2 g (0.404 mol) of sodium hydroxide and 0.6 g of triethyl amine in 0.2 liter of water, is added dropwise at −5° to +3° C in the same way as described in Example 1. On completion of the reaction, the reaction mixture has a pH-value of 6.7. The dicyanate precipitated is filtered under suction and washed first thoroughly with water and then with 3 × 50 ml portions of isopropanol and dried in air. Yield: 51 g (92% of the theoretical), m.p.: 82° C.

EXAMPLE 5

113.6 g (0.4 mol) of 2,2-bis-(3,5-dimethyl-4-hydroxy phenyl)-propane, 46.1 g (0.82 mol) of potassium hydroxide in 120 g of water and 120 g of isopropanol are added dropwise with stirring at −5° to +3° C to a mixture of 250 ml of isopropanol and 54 g (0.88 mol) of cyanogen chloride. On completion of the reaction, the crystalline sludge formed is filtered under suction, washed thoroughly with water and then with a little cold isopropanol. 119 g (90% of the theoretical) of dicyanate are obtained after drying in air. m.p.: 134°-135° C.

What we claim is:

1. A process for producing a polyfunctional aromatic cyanic acid ester which compirses reacting at least one aromatic hydroxy salt selected from the group consisting of alkaline earth and alkali metal salts of aromatic polyhydroxy compounds in the presence of aqueous isopropanol as solvent and from 0.001 to 10% by weight, based on the weight of said aromatic hydroxy salt, of a catalytic tertiary amine with excess cyanogen halide, said aromatic hydroxy salt having been produced by reacting a polyhydroxy compound with an excess of up to 0.1 mol of aromatic hydroxy groups of at least one metal compound of the group consisting of alkaline earth and alkali metal compounds and said cyanogen halide excess comprised up to 1 mol per mol of aromatic hydroxy groups plus the excess mols of said metal compound used for producing said aromatic hydroxy salt plus 1.1% by weight of cyanogen halide for each percent by weight of the catalytic tertiary amine used.

2. The process of claim 1 wherein the reaction is carried out at a temperature of from −40° to 65° C.

* * * * *